United States Patent [19]

Ekeze et al.

[11] Patent Number: 5,702,884
[45] Date of Patent: Dec. 30, 1997

[54] WHOLE BLOOD SAMPLE PREPARATION FOR POLYMERASE CHAIN REACTION USING AMMONIUM CHLORIDE AND A CARBOXYLIC ACID OR METAL CARBOXYLATE FOR SELECTIVE RED BLOOD CELL LYSIS

[75] Inventors: Tobias E. Ekeze, Brockport; JoAnne Hansen Kerschner, Rochester, both of N.Y.

[73] Assignee: Johnson & Johnson Clinical Diagnostics, Inc., Rochester, N.Y.

[21] Appl. No.: 615,848

[22] Filed: Mar. 12, 1996

[51] Int. Cl.$^6$ .............. C12Q 1/70; C12P 19/34; C07H 21/04
[52] U.S. Cl. .............. 435/5; 435/91.2; 435/6; 536/24.3; 536/24.32; 424/534
[58] Field of Search .............. 435/5, 6, 41.2; 536/24.3, 24.32; 424/534

[56] References Cited

U.S. PATENT DOCUMENTS

| | | | |
|---|---|---|---|
| 4,407,942 | 10/1983 | Birnboim | 435/6 |
| 4,683,195 | 7/1987 | Mullis | 435/6 |
| 5,300,635 | 4/1994 | Macfarlane | 536/25 |

Primary Examiner—Kenneth R. Horlick
Assistant Examiner—Joyce Tung

[57] ABSTRACT

Leucocytes can be quickly and selectively separated from erythrocytes by subjecting a whole blood sample to a series of steps including lysing the erythrocytes and washing the remaining leucocytes with a solution containing ammonium chloride and a carboxylic acid or a metal carboxylate. The resulting white blood cells can be readily lysed and subjected to polymerase chain reaction to amplify and detect a target nucleic acid. The test kit useful in practicing the amplification method includes a labeled primer, a PCR reagent and a reagent mixture containing ammonium chloride and a carboxylic acid or a metal carboxylate for sample preparation.

21 Claims, No Drawings

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: modified_base
        ( B ) LOCATION: 1
        ( D ) OTHER INFORMATION: /label=OTHER

```
            /  note="Base modified with a biotinyl moiety"

( x i ) SEQUENCE DESCRIPTION: SEQ ID NO:1:

ATAATCCACC TATCCCAGTA GGAGAAAT                                          2 8

( 2 ) INFORMATION FOR SEQ ID NO:2:

( i ) SEQUENCE CHARACTERISTICS:
                ( A ) LENGTH: 28 base pairs
                ( B ) TYPE: nucleic acid
                ( C ) STRANDEDNESS: single
                ( D ) TOPOLOGY: linear ( i i ) MOLECULE TYPE: DNA (genomic)

( i x ) FEATURE:
                ( A ) NAME/KEY: modified_base
                ( B ) LOCATION: 1
                ( D ) OTHER INFORMATION: /mod_base=OTHER
                            /  note="Based modified with a biotinyl moiety"

( x i ) SEQUENCE DESCRIPTION: SEQ ID NO:2:

TTTGGTCCTT GTCTTATGTC CAGAATGC                                          2 8

( 2 ) INFORMATION FOR SEQ ID NO:3:

( i ) SEQUENCE CHARACTERISTICS:
                ( A ) LENGTH: 41 base pairs
                ( B ) TYPE: nucleic acid
                ( C ) STRANDEDNESS: single
                ( D ) TOPOLOGY: linear ( i i ) MOLECULE TYPE: DNA (genomic)

( i x ) FEATURE:
                ( A ) NAME/KEY: modified_base
                ( B ) LOCATION: 41
                ( D ) OTHER INFORMATION: /mod_base=OTHER
                            /  note="Based modified with two tetraethylene glycol
                                spacers connected to a single aminediol linking group"

( x i ) SEQUENCE DESCRIPTION: SEQ ID NO:3:

ATCCTGGGAT TAAATAAAAT AGTAAGAATG TATAGCCCTA C                           4 1
```

WHOLE BLOOD SAMPLE PREPARATION FOR POLYMERASE CHAIN REACTION USING AMMONIUM CHLORIDE AND A CARBOXYLIC ACID OR METAL CARBOXYLATE FOR SELECTIVE RED BLOOD CELL LYSIS

BACKGROUND INFORMATION

1. Field of the Invention

This invention relates to a method for preparing a whole blood sample for polymerase chain reaction (PCR) by separating leucocytes from erythrocytes. It also relates to a method for amplification of a target nucleic acid isolated from the prepared leucocytes, and to a kit useful in practicing the method.

2. Background of the Invention

Technology to detect quantities of nucleic acids has advanced rapidly over the last two decades including the development of highly sophisticated hybridization assays using probes in amplification techniques such as PCR. Researchers have readily recognized the value of such technology to detect diseases and genetic features in human or animal test specimens. The use of probes and primers in such technology is based upon the concept of complementarity, that is, the bonding of two strands of a nucleic acid by hydrogen bonds between complementary nucleotides (also known as nucleotide pairs).

PCR is a significant advance in the art to allow detection of very small concentrations of a targeted nucleic acid. The details of PCR are described, for example, in U.S. Pat. No. 4,683,195 (Mullis et al), U.S. Pat. No. 4,683,202 (Mullis) and U.S. Pat. No. 4,965,188 (Mullis et al), although there is a rapidly expanding volume of literature in this field. Without going into extensive detail, PCR involves hybridizing primers to the strands of a targeted nucleic acid (considered "templates") in the presence of a polymerization agent (such as DNA polymerase) and deoxyribonucleoside triphosphates under the appropriate conditions. The result is the formation of primer extension products along the templates, the products having added thereto nucleotides which are complementary to the templates.

Once the primer extension products are denatured, and one copy of the templates has been prepared, the cycle of priming, extending and denaturation can be carried out as many times as desired to provide an exponential increase in the amount of nucleic acid which has the same sequence as the target nucleic acid. In effect, the target nucleic acid is duplicated (or "amplified") many times so that it is more easily detected.

In order to effectively amplify and detect a target nucleic acid, it is usually necessary to isolate that nucleic acid from cellular and other specimen debris. For example, it is well known in the field that red blood cells inhibit PCR. Various lysing procedures are known, including freezing, treatment with digesting enzymes such as proteases (for example, Proteinase K), boiling, and use of detergents (see for example U.S. Ser. No. 178,202, filed Apr. 6, 1988 by Higuchi, and EP-A-0 428 197, published May 22, 1991).

It is also known that many target nucleic acids in whole blood are found in specific cell populations, such as in white blood cells (leucocytes) as opposed to the red blood cells (erythrocytes).

There are many known techniques used for the separation and purification of blood cell populations (and subpopulations). One of the most commonly used techniques for separating leucocytes from erythrocytes is to simply mix a sample of whole blood with a solution, comprising reagents which cause aggregation of the erythrocytes increasing their rate of sedimentation. Leucocytes are less affected by the sedimentation fluid so they can be collected from the upper part of the fluid when the erythrocytes have settled.

More recent techniques involve the use of erythrocyte aggregating agents, such as certain polymeric compounds (for example FICOLL™ 400), as described for example in U.S. Pat. No. 4,255,256 (Ferrante et al). It is also possible to aggregate certain subpopulations of the leucocytes as described in the Ferrante et al patent. Separation can also be achieved using dextran gradient techniques as described, for example, by Eggleton et al, *J. Immun. Methods* 121, pp. 105–113 (1989).

It has been found, however, that many techniques and reagents used for lysing erythrocytes interfere with polymerase chain reaction, and thus reduce its efficiency, this is especially problematic when the target nucleic acid is present in very low concentrations. Also some lysing agents such as lysing detergents may solubilize the membranes of the leucocytes, resulting in cytoplasmic DNA loss during cell separation. In addition, cells prepared using various lysing agents are not viable and cannot be cultured. To avoid these problems, it is necessary to use compounds that will selectively lyse erythrocytes without compromising the integrity of the leucocytes.

One such selective lysing compound is ammonium chloride, as described for example in U.S. Pat. No. 4,407, 942 (Birnboim) and by Eggleton et al *J. Immun. Methods* 121, pp. 105–113 (1989). Typically, after use of ammonium chloride, the lysed material is removed by centrifugation, leaving the leucocytes for further treatment. However, the protocols for using ammonium chloride taught in the art are not always sufficient. Eggleton et al, for example, lysed erythrocytes with ice cold ammonium chloride and then washed the leucocytes with buffer until they were further used. While it was important to maintain the viability of the leucocytes, they were still subject to lysis using the Eggleton et al procedure.

Such procedures are not as useful for isolating target nucleic acids for polymerase chain reaction, particularly when the leucocyte population contains a low titer of the target nucleic acid. Premature lysis of the white blood cells may result in significant loss of target nucleic acid. Moreover, the Eggleton et al procedure takes too long (over 40 minutes) for a commercially useful cell preparatory method.

SUMMARY OF THE INVENTION

The problems noted above are overcome with the method for the selective preparation of leucocytes of the present invention. The method comprises:

A) mixing a whole blood sample with an erythrocyte lysing solution comprising at least about 50 mM of ammonium chloride and between about 0.001 weight percent and about 0.1 weight percent of a carboxylic acid or a metal carboxylate having at least one carboxyl group, wherein the carboxylic acid or metal carboxylate has structural formula:

wherein M is hydrogen or a monovalent cation, and

R is an alkyl of 1 to 6 carbon atoms, a substituted alkyl of 1 to 6 carbon atoms, a substituted alkenyl of 2 to 6 carbon atoms, an aryl, a substituted aryl, an arylalkyl, or a substituted arylalkyl, and wherein the lysing solution has a pH of between 6 and 8, B) centrifuging the resulting mixture to form a pellet of leucocytes from the whole blood sample, C) after removing the supernatant, washing the leucocyte pellet in a fresh sample of the lysing solution and D) centrifuging and isolating the leucocyte pellet, provided that steps A) through D) are carried out within about 20 minutes.

This invention also provides a method for the amplification and detection of a target nucleic acid comprising:

I) selectively preparing leucocytes suspected of containing a target nucleic acid in a whole blood sample by:

A) mixing a whole blood sample with an erythrocyte lysing solution comprising at least about 50 mM of ammonium chloride and between about 0.001 weight percent and about 0.1 weight percent of a carboxylic acid or a metal carboxylate having at least one carboxyl group, wherein the carboxylic acid or metal carboxylate has structural formula:

R—COOM wherein M is hydrogen or a monovalent cation, and

R is an alkyl of 1 to 6 carbon atoms, a substituted alkyl of 1 to 6 carbon atoms, a substituted alkenyl of 2 to 6 carbon atoms, an aryl, a substituted aryl, an arylalkyl, or a substituted arylalkyl, and wherein the lysing solution has a pH of between 6 and 8, B) centrifuging the resulting mixture to form a pellet of leucocytes from the whole blood sample, C) after removing the supernatant, washing the leucocyte pellet in a fresh sample of the lysing solution and D) centrifuging and isolating the leucocyte pellet, provided that steps A) through D) are carried out within about 20 minutes, II) lysing the leucocytes in the washed pellet to release the target nucleic acid, III) amplifying the released target nucleic acid using polymerase chain reaction and a set of primers that are specific to and hybridizable with opposing strands of the target nucleic acid, and IV) detecting the amplified target nucleic acid.

A kit for polymerase chain reaction comprising:

a) a set of two primers specific to and hybridizable with opposing strands of a target nucleic acid, one or both of the primers being labeled with a detection moiety, and in the same or different package, at least one additional PCR reagent, and b) in a separate package, a solution or a dry composition containing, when the dry composition is reconstituted with water, at least about 50 mM of ammonium chloride and at least about 0.005 weight percent of a carboxylic acid or a metal carboxylate, having at least one carboxyl group, wherein the carboxylic acid or metal carboxylate has structural formula:

R—COOM wherein M is hydrogen or a monovalent cation, and

R is an alkyl of 1 to 6 carbon atoms, a substituted alkyl of 1 to 6 carbon atoms, an alkenyl of stole carbon atoms, a substituted alkenyl of 2 to 6 carbon atoms, an aryl, a substituted aryl, an arylalkyl, or a substituted arylalkyl, and wherein the solution has a pH of between 6 and 8.

The present invention provides a rapid and effective method for selectively preparing leucocytes from a whole blood sample for amplification and detection of a target nucleic acid. The preparatory method can be carried out within about 20 minutes (preferably, within 15 minutes) even for target nucleic acids that are present in very low concentrations. Moreover, the method can be carried out at room temperature as the viability of the separated leucocytes is not a concern for polymerase chain reaction. Both nuclear and cytoplasmic DNA are retained using the preparatory method of this invention.

These advantages are achieved by using a solution comprising ammonium chloride and a carboxylic acid or a metal carboxylate to selectively lyse erythrocytes, and using the same solution to wash the separated leucocytes before they are lysed to release target nucleic acid. Merely using an ammonium chloride solution to lyse the erythrocytes is often not sufficient in providing an adequate leucocyte titer containing target nucleic acids which will be used for amplification and detection.

DETAILED DESCRIPTION OF THE INVENTION

The present invention is especially suited for extraction and detection of one or more target nucleic acids present in a whole blood sample collected from animals or humans. Since the target nucleic acid typically resides in certain cells (leucocytes) of the sample, steps are taken to separate those cells intact from the rest of the sample according to this invention.

The whole blood sample is firstly mixed with a buffered erythrocyte lysing solution comprising ammonium chloride and a carboxylic acid or a metal carboxylate in a suitable container. Carboxylic acids and metal carboxlyates suitable for use in the present invention have at least one carboxyl group and have the structural formula:

R—COOM wherein M is hydrogen or a monovalent cation (such as, sodium, potassium or lithium), and R is an alkyl of 1 to 6 carbon atoms (such as methyl, ethyl, butyl, isobutyl, propyl, isopropyl, and the like), a substituted alkyl [for example, a haloalkyl of 1 to 6 carbon atoms (such as, bromomethyl, chloromethyl, fluoromethyl, 1,1-dichlorolmethyl, 1,1,1-trichloromethyl, 1,1,1-trifluromethyl, 2,2,2-trichlorolethyl, and the like), an alkoxyalkyl of 2 to 6 carbon atoms (such as, methoxymethyl, methoxyethyl and the like), a hydroxyalkyl of 1 to 6 carbon atoms (such as, hydroxymethyl, 1-hydroxyethyl, 2-hydroxyethyl, 2,3-hydroxyethyl, and the like), an aminoalkyl of 1 to 6 carbon atoms (such as, aminomethyl, 2-aminoethyl, 3-aminoethyl, 3-aminopropyl, 2,4-diaminobutyl, methylaminomethyl, 4-aminobutyl, and the like)], an alkenyl of 2 to 6 carbon atoms (such as, ethenyl, 1-propenyl, isopropenyl, and 2-butenyl, and the like), a substituted alkenyl of 2 to 6 carbon atoms, an aryl, a substituted aryl (such as, phenyl, 2-methoxyphenyl, 3-methoxyphenyl, 4-methoxyphenyl, 4-aminophenyl, 2-chlorophenyl, 4-chlorophenyl, and the like), an arylalkyl, or a substituted arylalkyl.

Preferably, R is substituted or unsubstituted alkyl of 1 to 4 carbon atoms, more preferably of 1 to 3 carbon atoms.

Even more preferably, R is a substituted methyl, such as a halogen substituted methyl. Most preferably, R is methyl. Thus, examples of preferred carboxylic acids include monohalo acetic acid, dihalo acetic acid, trihalo acetic acid, and acetic acid, and metal carboxylates thereof.

The erythrocyte lysing solution contains from about 50 to about 100 mM of ammonium chloride. The carboxylic acid or metal carboxylate is present in the solution at about 0.001 to about 0.1 weight percent. Preferably, the lysing solution contains from about 0.005 to about 0.05 weight percent of a carboxylic acid or a metal carboxylate.

The carboxylic acids and metal carboxylates of this invention are generally available commercially as the free acid or as the metal carboxylate, or may be made synthetically by procedures which are well known to skilled artisans. Examples of commercially available carboxylic acids of the instant invention include the following available from Eastman Organic Chemicals (Kingsport, Tenn.): acetic acid, benzoic acid, p-aminobenzoic, 1,1,1- trichloroacetic acid, 2-methoxybenzoic acid, 4-chlorophenyl, 2-bromo-3-methylbutyric acid, isobutyric acid, cyanoacetic acid, 2-butenoic acid, 1,3-dicarboxylbenzene, 2-ethylbutyric acid, trans-cinnamic acid, and others. Those cited and others are also available from other suppliers and manufacturers, such as TCI America (Portland, Oreg.), Sigma Chemical Company (St. Louis, Mo.), ICN (Irvine, Calif.) and many others that are well known to skilled artisans.

The volume ratio of whole blood sample to the erythrocyte lysing solution used in the present invention is from about 1:1 to about 1:10. Preferably, the ratio is from about 1:1 to about 1:5. More preferably, the ratio is about 1:4. The whole blood sample can have any desired volume, but generally it is from about 0.1 to about 10 ml.

The lysing solution used in the present invention is generally composed of ammonium chloride and a carboxylic acid or a metal carboxylate in a suitable buffer which provides a pH in the range of from about 6.0 to about 8.0 (preferably from about 6.5 to about 7.5). Useful buffers include, but are not limited to, sodium bicarbonate, tris (hydroxymethyl)aminomethane hydrochloride, phosphate and others known in the art. The solution can optionally contain ion chelating agents, such as ethylenediaaminetetraacetic acid and others known to one skilled in the art.

Mixing is carried out for up to about 10 minutes (preferably about 5 minutes) at room temperature in order to allow the lysing solution to lyse the erythrocytes.

The resulting mixture is centrifuged for up to 10 minutes (preferably for about 5 minutes) using a conventional centrifuge to separate the leucocytes (in a pellet) from the supernatant containing the products of lysing and other unwanted debris.

After removing the supernatant, the pellet of leucocytes is washed at least once at room temperature with a fresh sample of the lysing solution, followed by a second centrifugation at room temperature for up to about 10 minutes (preferably about 5 minutes). Upon isolating the leucocyte pellet again, the leucocytes are available for further handling (for example, lysing prior to polymerase chain reaction). The entire method of isolating the leucocytes requires about 20 minutes at most, and preferably takes from about 10 to about 16 minutes. Fifteen minutes is most preferred.

The isolated leucocytes can be used for a number of purposes readily apparent to workers in the biological and medical arts. For example, they can be used to study the functions of various leucocyte cells (perhaps requiring further fractionation of subpopulations), for the preparation of human gamma interferon (for example, as in U.S. Pat. No. 4,696,899 of Toth et al), for determining the T4/T8 cell ratio (for example, as in U.S. Pat. No. 4,826,760 of Privitera), for culturing viruses, and for preparing vaccines (for example, as in U.S. Pat. No. 4,956,278 of Hart et al). Preferably, the leucocytes are separated in preparation for polymerase chain reaction, as described in more detail below.

The general principles and conditions for amplification and detection of nucleic acids using polymerase chain reaction are quite well known, the details of which are provided in numerous references including U.S. Pat. No. 4,683,195, U.S. Pat. No. 4,683,202, U.S. Pat. No. 4,965,188 and WO-A-91/12342 and by Guatelli et al, *Clin. Microbiol. Rev.*, 2 (2), pp. 217–226 (1989). The noted U.S. patents are incorporated herein by reference. In view of the teaching in the art and the specific teaching provided herein, a worker skilled in the art should have no difficulty in practicing the present invention by combining the leucocyte preparatory method of this invention with polymerase chain reaction procedures.

The present invention is directed to the amplification or detection of one or more specific nucleic acid sequences present in one or more target nucleic acids in a specimen of whole blood.

The present invention is especially useful for producing, in exponential quantities relative to the number of reaction steps involved, at least one specific nucleic acid sequence associated with an infectious agent present in leucocytes. The product will be a discrete nucleic acid duplex with termini corresponding to the ends of the specific primers employed. Moreover, a plurality of target nucleic acids can be amplified and detected simultaneously by using a corresponding set of primers and detection means for each specific nucleic acid. Multiple sequences in the same nucleic acid can also be amplified and detected. The present invention is particularly useful for the amplification and detection of target nucleic acids found in bacterial DNA, fungal DNA, viral RNA, or DNA found in bacterial or virus-infected leucocytes.

The method described herein can be used to detect specific nucleic acid sequences associated with infectious diseases, genetic disorders or cellular disorders such as cancers or any other disease states not specifically included in these categories. It may also be used in forensic investigations and DNA typing. For purposes of this invention, genetic diseases include specific deletions or mutations in genomic DNA from any organism, such as sickle cell anemia, cystic fibrosis, α-thalassemia, β-thalessemia and others readily apparent to one skilled in the art. Human Leukocyte Antigen (HLA) can be categorized with the present invention. Bacteria which can be detected include, but are not limited to, bacteria which may be found in the blood, Salmonella, Streptococcus species, Chlamydia species, Gonococcus species, mycobacteria species (such as *Mycobacterium tuberculosis* and *Mycobacterium avium* complex), Mycoplasma species (such as Mycoplasma Haemophilus influenzae and *Mycoplasma pneumoniae*), *Legionella pneumophila*, *Borrelia burgdorferei*, *Pneumocystis carinii*, *Clostridium difficile*, Campylobacter species, Yersinia species, Shigella species and Listeria species. Viruses which are detectable include, but are not limited to, herpes simplex viruses, Epstein Barr virus, respiratory syncytial viruses, hepatitis viruses and retroviruses syncytial viruses, hepatitis viruses and retroviruses (such as HTLV-I, HTLV-II, HIV-I and HIV-II). Protozoan parasites and fungi (including yeasts and molds) are also detectable. Other detectable species would be readily apparent to one skilled in the art. The invention is particularly useful for the detection of the presence of DNA associated with various bacteria or viruses.

As used herein in referring to primers or probes, the term "oligonucleotide" refers to a molecule comprised of two or more deoxyribonucleotides or ribonucleotides, and preferably more than three. Its exact size is not critical but depends upon many factors including the ultimate use or function of the oligonucleotide. The oligonucleotide may be derived by any method known in the art.

A "PCR reagent" refers to any of the reagents considered essential to PCR, namely one or more primers for the target nucleic acid, a DNA polymerase, a DNA polymerase cofactor, and one or more deoxyribonucleoside-5'-triphosphates.

The term "primer" refers to an oligonucleotide, whether naturally occurring or synthetically produced, which is capable of acting as a point of initiation of synthesis when placed under conditions in which synthesis of a primer extension product complementary to a nucleic acid strand (that is, template) is induced. Such conditions include the presence of nucleotides (such as the four standard deoxyribonucleoside-5'-triphosphates), a DNA polymerase and DNA polymerase cofactor, and suitable temperature and pH.

The primer is long enough to prime the synthesis of extension products in the presence of the DNA polymerase. The exact size of each primer will vary depending upon the use contemplated, the complexity of the targeted sequence, reaction temperature and the source of the primer. Generally, the primers used in this invention will have from 12 to 60 nucleotides, and preferably, they have from 18 to 45 nucleotides.

The primers used in the present invention are selected to be "substantially complementary" to the different strands of each specific sequence to be amplified. This means that they must be sufficiently complementary to hybridize with their respective strands to form the desired hybridized products and then be extendable by a DNA polymerase. In the preferred and most practical situation, the primer has exact complementarity to the target nucleic acid.

Primers useful herein can be obtained from a number of sources or prepared using known techniques and equipment, including for example, an ABI DNA Synthesizer (available from Applied Biosystems) or a Biosearch 8600 Series or 8800 Series Synthesizer (available from Milligen-Biosearch, Inc.) and known methods for their use (for example as described in U.S. Pat. No. 4,965,188). Naturally occurring primers isolated from biological sources are also useful (such as restriction endonuclease digests). As used herein, the term "primer" also refers to a mixture of primers.

One or both primers can be labeled, with the same or different label, for detection. Procedures for attaching labels and preparing primers are well known in the art, for example, as described by Agrawal et al, Nucleic Acid Res., 14, pp. 6227–45 (1986), U.S. Pat. No. 4,914,210 (Levenson et al) relating to biotin labels, U.S. Pat. No. 4,962,029 (Levenson et al) relating to enzyme labels, and the references noted therein. Useful labels also include radioisotopes, electron-dense reagents, chromogens, fluorogens, phosphorescent moieties, ferritin and other magnetic particles (see U.S. Pat. No. 4,795,698 of Owen et al and U.S. Pat. No. 4,920,061 of Poynton et al), chemiluminescent moieties (such as luminol), and other specific binding species (avidin, streptavidin, biotin, sugars or lectins). Preferred labels are enzymes, radioisotopes and specific binding species (such as biotin). Useful enzymes include, glucose oxidase, peroxidases, uricase, alkaline phosphatase and others known in the art and can be attached to oligonucleotides using known procedures. Reagents to provide a colorimetric or chemiluminescent signal with such enzymes are well known.

Where the label is an enzyme such as a peroxidase, at some point in the assay, hydrogen peroxides and suitable dye-forming compositions are added to provide a detectable dye. For example, useful dye-providing reagents include tetramethylbenzidine and derivatives thereof, and leuco dyes, such as water-insoluble triarylimidazole leuco dyes (as described in U.S. Pat. No. 4,089,747 of Bruschi), or other compounds which react to provide a dye in the presence of peroxidase and hydrogen peroxide. Particularly useful dye-providing compositions are described in EP-A-0 308 236 (published Mar. 22, 1989). Chemiluminescent signals in response to a peroxidase label can also be generated using the appropriate reagents.

If one or both primers are biotinylated, the amplified nucleic acid can be detected using detectably labeled avidin or an equivalent thereof (such as streptavidin). For example, avidin can be conjugated with an enzyme, or have a radioisotope using known technology. Biotin on the amplified product complexes with the avidin, and appropriate detection techniques to detect a radioactive, colorimetric or chemiluminescent signal are used.

As used herein, a capture "probe" is an oligonucleotide which is substantially complementary to a nucleic acid sequence of one or more strands of the target nucleic acid, and which is used to insolublize the amplified nucleic acid. The probe oligonucleotide is generally attached to a suitable water-insoluble substrate such as polymeric or glass beads, microtiter plate well, thin polymeric or cellulosic film or other materials readily apparent to one skilled in the art. The oligonucleotide is generally from about 12 to about 40 nucleotides in length, although the length is not critical.

A DNA polymerase is an enzyme which will add deoxynucleoside monophosphate molecules to the 3'-hydroxy end of the primer in a complex of primer and template, but this addition is in a template dependent manner (that is, dependent upon the specific nucleotides in the template). Many useful DNA polymerases are known in the art. Preferably, the polymerase is "thermostable", meaning that it is stable to heat and preferentially active at higher temperatures, especially the high temperatures used for denaturation of DNA strands. More particularly, the thermostable DNA polymerases are not substantially inactivated by the high temperatures used in PCR as described herein. Such temperatures will vary depending upon a number of reaction conditions, including pH, the nucleotide composition of the target nucleic acid and primers, the length of primer, salt concentration and other conditions known in the art.

A number of thermostable DNA polymerases have been reported in the art, including those mentioned in detail in U.S. Pat. No. 4,965,188 (Mullis et al) and U.S. Pat. No. 4,889,818 (Gelfand et al). Particularly useful polymerases are those obtained from various Thermus bacterial species, such as *Thermus aquaticus, Thermus thermophilus, Thermus filiformis* or *Thermus flavus*. Other useful thermostable polymerases are obtained from a variety of other microbial sources including *Thermococcus literalis, Pyrococcus furiosus,* Thermotoga sp. and those described in WO-A-89/06691 (published Jul. 27, 1989). Some useful polymerases are commercially available. A number of techniques are known for isolating naturally-occurring polymerases from organisms, and for producing genetically engineered enzymes using recombinant techniques, as noted in the art cited in this paragraph. A preferred method for preparing a DNA polymerase equivalent to that obtained from *Thermus aquaticus* is described in EP-A-0 482 714 (published Apr. 29, 1992).

A DNA polymerase cofactor refers to a nonprotein compound on which the enzyme depends for activity. Thus, the enzyme is datalytically inactive without the presence of the cofactor. The exact mechanism of the interaction of the cofactor with the polymerase is unknown at present. A number of such materials are known cofactors including manganese and magnesium compounds. Such compounds contain the manganese or magnesium in such a form that divalent anions are released into an aqueous solution. Useful cofactors include, but are not limited to, magnanese and magnesium salts, such as chlorides, sulfates, acetates and fatty acid salts (for example, butyric, caproic, caprylic, capric and lauric acid salts). The smaller salts, that is chlorides, sulfates and acetates, are preferred.

Magnesium salts, such as magnesium chlorides and sulfates are most preferred in the practice of the invention.

Also needed for PCR is a deoxyribonucleotide-5' triphosphate, such as dATP, dCTP, dGTP, dUTP or dTTP. Usually, dATP, dCTP, dGTP and dTTP are all used in PCR. Analogues such as dITP and 7-deaza-dGTP are also useful.

Each PCR reagent can be supplied individually packaged, or in a mixture with one or more other PCR reagents, including primers, DNA polymerase cofactors and deoxyribonucleoside-5'-triphosphates, all in a suitable buffer. Representative buffers include, but are not limited to tris(hydroxymethyl)aminomethane (which is preferred), N,N-bis(2-hydroxyethyl)-2-aminoethanesulfonic acid, 4-(2-hydroxyethyl)-1-piperazinethanesulfonic acid, N-(2-hydroxyethyl)piperazine-N'-(2-hydroxypropanesulfonic acid), 3-(N-morpholino)propanesulfonic acid and N-[tris(hydroxymethyl)methyl]-2-aminoethanesulfonic acid.

Since the nucleic acid to be amplified or detected is usually in double stranded form, the two strands must be separated (that is, denatured before priming can take place). This can occur during the extraction process, or be a separate step afterwards. Denaturation is accomplished using a heat treatment alone or in combination with any suitable other physical, chemical or enzymatic means as described in the art. Initial denaturation is generally carried out by heating the specimen suspected of containing the targeted nucleic acid at a first temperature of from about 85° to about 100° C. for a suitable time, for example from about 1 second to 3 minutes.

The denatured strands are then cooled to a temperature which is generally in the range of from about 55° to about 70° C. The time needed for cooling the denatured strands will vary depending upon the type of apparatus used for the PCR process.

Once the denatured strands are cooled, the reaction mixture containing the PCR reagents is incubated at a suitable temperature to effect formation of primer extension products. Generally, this temperature is at least about 50° C., and preferably in the range of from about 65° to about 75° C. In some embodiments, one temperature is used for priming and another temperature for primer extension. In a preferred embodiment, the same temperature is used for both priming and primer extension. The time for incubation can vary widely depending upon the incubation temperature, but in preferred embodiments, it is from about 1 to about 120 seconds.

The primer extension products thus formed can be detected in a suitable manner while as hybridized products, or denatured either for detection of one or both strands, or for further cycling in PCR.

If the hybridized primer extension products are denatured, PCR can be carried out further in as many cycles of forming primer extension products and denaturation as desired. Generally, at least 20 cycles will be carried out, with from 20 to 50 cycles being preferred.

After denaturation the last time in the assay, the final primer extension products can be detected, as described below.

The amplification method of this invention is preferably conducted in a continuous, automated manner so that the reaction mixture is temperature cycled in a controlled manner for desired preset times. A number of instruments have been developed for this purpose, as one of ordinary skill in the art would know.

One such instrument for this purpose is described in some detail in U.S. Pat. No. 4,965,188 and EP-A-0 236 069, and involves moving liquids from one temperature environment to another under controlled conditions.

Another instrument utilizes temperature cycling without a liquid handling system, and is described in some detail in U.S. Pat. No. 4,965,188 and EP-A-0 236 069. Generally, this instrument includes a heat conducting container for holding a number of reaction tubes containing reaction mixture, a means for heating, cooling and temperature maintenance, and a computing means to generate signals to control the amplification sequence, changes in temperature and timing.

A gas chromatograph has also been used for amplification, as described for example by Hoffman et al, *Biotechniques*, 6(10), pp. 932–936 (1988), and amplification in a "teacup" has been described as a simple and inexpensive technique [Innis et al (Eds.), *PCR Protocols: A Guide to Methods and Applications*, Chapter 51, pp. 429–434 by Robert Watson, Academic Press, Inc., 1990].

A preferred instrument for processing amplification reactions in a disposable chemical test pack is described in some detail in EP-A-0 402,994 (published Dec. 19, 1990). In general, this instrument comprises a surface for supporting a chemical test pack, pressure applicators supported above the surface for acting on the reaction pack to transfer fluids between adjacent chambers in the test pack, and means for operating the pressure applicators through a range of movements extending across the test pack.

EP-A 0 402,994 provides details of useful chemical test packs which can be processed using the instrument described in that same publication. Also described therein are means for heating and cooling the test pack at repeated intervals (that is, through cycles) appropriate for the method of the present invention. As noted above, while these instruments and test packs are preferred in practicing the present invention, they are not considered essential to obtain the beneficial results noted herein.

It is also useful for the method of this invention to be carried out in a suitable container. The most crude container would be a test tube, cuvette, flask or beaker, but more sophisticated containers have been fashioned in order to facilitate automated procedures for performing the method (see for example, WO-A-91/12342). For example, cuvette and chemical test packs (also known as pouches), constructed to provide certain temperature characteristics during the practice of the method, are described in U.S. Pat. No. 4,902,624 (Columbus et al) and EP-A-0 381,501 (published Aug. 8, 1990). Such test packs have a multiplicity of reaction chambers having various reagents, buffers and other materials which are useful at various stages in the amplification or detection method. The packs can be appropriately and rapidly heated and cooled in cycles to promote the various steps of the amplification method of this invention.

Other useful containers could be suitably fashioned for automated or single use of the method of this invention.

In order for the amplified product to be detected, it is often useful (but not necessary) for it to be separated from the other materials in the reaction medium. This is done by any of a number of ways, but preferably by using a water-insoluble capture probe so that the primer extension products which are replicated in the method are water-insolubilized and removed from the reagent mixture. Probes can be attached to insoluble materials in a suitable manner.

The amplified product can be separated from undesired materials by using an oligonucleotide complementary thereto, which oligonucleotide is attached to an insoluble substrate (such as polymeric or magnetic particles) using known attachment techniques to form the capture probe (noted above). One such technique is described in EP-A-0 439 222 (published Sep. 18, 1991). Other techniques are described for example in U.S. Pat. No. 4,713,326 (Dattagupta et al), WO-A-88/01302 (published Feb. 25, 1988) and EP-B-0 070 687 (published Jan. 26, 1983) whereby intermediate oligonucleotides are used in a hybridized product of multiple components to which the capture oligonucleotide and amplified nucleic acid are joined. Separation can be achieved by centrifugation or subjecting the mixture to a magnetic field.

Other useful separation means are microporous filtration membranes such as the polyamide membranes marketed by Pall Corp. (for example as LOPRODYNE™ or BIO-DYNE™ membranes). They can be used uncoated or pre-coated with surfactants or other materials which facilitate the analytical procedures.

The membranes can be used as a separate substrate with suitable containers for carrying out other steps of the assay. They can be mounted as part of a disposable test device. Various disposable test devices are known in the art including those described in U.S. Pat. No. 3,825,410 (Bagshawe), U.S. Pat. No. 3,888,629 (Bagshawe), U.S. Pat. No. 3,970,429 (Updike) and U.S. Pat. No. 4,446,232 (Liotta). Particularly useful devices are described in U.S. Pat. No. 4,921,677 (Hinckley et al) and are commercially available as SURE-CELL™ test devices and assay kits from Eastman Kodak Company.

Any useful solid support can be used for separation of water-insoluble products for detection, including a microtiter plate, test tube, beaker, beads, film, membrane filters, filter papers, gels, magnetic particles or glass wool. It can be made of a number of materials including glass, ceramics, metals, naturally occurring or synthetic polymers, cellulosic materials, filter materials and others readily apparent to one of ordinary skill in the art. Particularly useful solid support materials are polymeric beads generally having an average particle size of from about 0.1 to about 10 micrometers.

The detection can also be carried out by immobilizing a capture probe on a flat substrate, such as the microporous filtration membranes described above, or on thin polymeric films, film laminates, uncoated papers or polymer coated papers, a number of which are known in the art. Other details about such materials are provided in EP-A-0 408 738 (published Jan. 23, 1991).

The reagents, materials and instructions needed for carrying out the amplification method of this invention can be supplied in a test kit. Separate packaging or containers can be used for ammonium chloride and carboxylic acid or metal carboxylate, primers, PCR reagents, test devices (or test packs) and other materials generally required for the method. Preferably, the test kit includes the mixture of ammonium chloride and carboxylic acid or a metal carboxylate, all necessary PCR reagents, and a suitable container or test pack for carrying out the reactions.

The following examples are included to illustrate the practice of this invention, and are not meant to be limiting in any way. All percentages are by weight unless otherwise noted.

EXAMPLE 1

Preparation of Whole Blood Sample

This example compares the leucocyte number obtained after separation of leucocytes from erythrocytes and other materials in a whole blood sample using the erythrocyte lysing solution preparations and procedures described below.

Heparinized whole blood specimens were obtained from four different donors.

An aliquot (0.5 mL) of each specimen was mixed in a 1.5 mL microcentrifuge tube with 1 mL of a lysing solution (pH 7.2) containing in all cases 10 mM sodium bicarbonate and, A. 160 mM ammonium chloride (160 AC) or, B. 160 mM ammonium chloride and 0.01 weight percent acetic acid (160 AC/AA) or, C. 80 mM ammonium chloride (80 AC) or, D. 80 mM ammonium chloride and 0.01 weight percent acetic acid (80 AC/AA).

The microcentrifuge tubes containing the specimens in the above solutions were gently mixed at room temperature for 5 minutes using an automatic rocker. The tubes were then centrifuged for 5 minutes at 3000 rpm at ambient temperature. The supernatant containing lysed erythrocytes, soluble components and other material was discarded. The pellet, containing leucocytes, was resuspended in fresh lysing solution identical to the solution with which the specimen was originally mixed. The suspension was recentrifuged at 3000 rpm for 5 minutes at ambient temperature. The supernatant was discarded and the pellet was resuspended in 1 mL of PBS (phosphate buffered saline, pH 7.2, Sigma Chemical Company, product number P0261). An aliquot of the suspension containing the separated leucocytes was diluted 1:10 with fresh PBS. The entire method was carried out in about 15 minutes.

The presence of leucocytes was verified by microscopy and the cells were counted under a microscope using a hemocytometer chamber. Three replicate counts were obtained from each diluted and resuspended sample and the average count and standard deviation about the average was calculated. Combining the dilution factor with the hemocytometer correction factor (provided by the hemocytometer manufacturer), the average count obtained using the hemocytometer was converted to an estimate of the number of white blood cells per milliliter of whole blood in the original specimen. These estimated counts are shown below in Table 1 for the different ammonium chloride solutions indicated above.

TABLE 1

| Specimen | Average (Std. Dev) | | (Leucocytes/mL) × 10⁻⁶ | |
|---|---|---|---|---|
| | 160AC | 160AC/A | 80AC | 80AC/AA |
| 1 | 82(6.7) | 98(3.2) | 83(3.5) | 99(2.7) |
| 2 | 83(4.2) | 99(2.7) | 86(2.0) | 102(3.1) |
| 3 | 81(3.0) | 99(2.3) | 81(0.6) | 103(1.5) |
| 4 | 82(2.1) | 99(3.6) | 82(2.9) | 102(2.0) |

The results shown in Table 1 demonstrate that the recovery of leucocytes from the original specimen was significantly greater when the carboxylic acid, acetic acid, was present, with greatest recovery in the preferred embodiment (80 AC/AA). This is of particular advantage when the target nucleic acid may be present in very low titer in the cell population.

EXAMPLE 2

Method for Isolating, Amplifying and Detecting a Target Nucleic Acid

This example demonstrates the amplification and detection of HIV-I DNA released from leucocytes using the procedure for isolating white blood cells described in example 1.

The following materials and methods were used in this Example:

The primers used in this example had the following sequences. Both of the following primers are complementary to the gag region of HIV-I DNA.

| | |
|---|---|
| 5'-X-ATAATCCACC TATCCCAGTA GGAGAAAT-3' | SEQ ID NO: 1: |
| 5'-X-TTTGGTCCTT GTCTTATGTC CAGAATGC-3' | SEQ ID NO: 2: |

In the primers, X represents a biotinyl moiety (derived from a biotin phosphoramidite reagent, DuPont) appended to the oligonucleotide through two aminotetraethylene glycol spacer groups using the technology described in U.S. Pat. No. 4,962,029 (Levenson et al).

The capture probe used in this example had the following sequence.

| | |
|---|---|
| 5'-ATCCTGGGAT TAAATAAAAT AGTAAGAATG TATAGC-CCTA C-Y-3' | SEQ ID NO: 3: |

"Y" represents two tetraethylene glycol spacers connected to a single aminediol linking group using the teaching of U.S. Pat. No. 4,914,210 (Levenson et al).

The primers and capture probe were prepared using known starting materials and procedures using an Applied Biosystems Model 380B, three column DNA synthesizer, standard phosphoramidite chemistry and the ABI 1 μmolar scale, fast cycle protocol. Nucleoside-3'-phosphoramidites and nucleoside derivatized controlled pore glass supports were obtained from Applied Biosystems. All purifications were carried out using a nucleic acid purification column, followed by reverse phase HPLC techniques.

To form capture reagents, the probes were covalently attached to polymeric particles (1 μm average diameter) prepared, using conventional emulsion techniques, from poly[styrene-co-3-(p-vinylbenzylthio)propionic acid] (95:5 weight ratio, 1 μm average diameter). A suspension of the particles in water was washed with 2-(N-morpholino) ethanesulfonic acid buffer (0.1 molar, pH 6), and suspended to about 10% solids. A sample (3.3 mL) of the washed particles, diluted to 3.33% solids in the buffer (0.1 molar, was mixed with 1-(3-dimethylaminopropyl)-3-ethylcarbodiimide hydrochloride (2.1 mL of 84 mg/mL water) and the probe (983 μL of 44.44 OD/mL nanopure water). The resulting suspension was heated at 50° C. in a water bath for about two hours with intermittent mixing and centrifuged. The particles were then washed three times with tris(hydroxymethyl)aminomethane buffer (0.01 molar, pH 8) containing (ethylenedinitrilo)tetraacetic acid disodium salt (0.1 mmolar) and resuspended therein to 4% solids.

Upon dilution to 0.25% solids with buffer, the capture reagents (1.2 μL) were applied to and dried in defined regions of the microporous membranes (LOPRODYNE-polyamide membrane, 5 μm average pore Size, from Pall Corp.) in the test wells of SURECELL™ disposable test devices (available from Johnson & Johnson Clinical Diagnostics Company), which are described in detail in U.S. Pat. No. 4,948,561 (Hinckley et al).

PCR was carried out using an automated Johnson & Johnson Clinical Diagnostics Company PCR processor which is described in detail in U.S. Pat. No. 5,089,233, incorporated herein by reference, using the heating and cooling protocol described below.

Recombinant DNA polymerase from Thermus aquaticus was obtained using conventional procedures.

Glycerol, tris(hydroxymethyl)aminomethane buffer and the dNTP's were obtained from Sigma Chemical.

Whole blood from patients who were sero-positive for HIV (specimen Nos. 1–10) and sero-negative for HIV (specimens 11 and 12) was obtained from a local hospital. The whole blood was treated according to the method of Example 1 in order to lyse erythrocytes and isolate white blood cells, using the lysing solution, D, of Example 1. The DNA from the white blood cells was extracted from the white blood cell pellet that was obtained subsequent to the second wash step.

The extraction of the DNA from the white blood cells was accomplished using a DNA polymer capture technique as described in pending U.S. Ser. No. 08/306,870 (filed Sep. 15, 1994) incorporated herein by reference. Briefly, 150 uL of a leukocyte lysing solution containing 10 mM tris (hydroxymethyl)aminomethane buffer, 0.15% of the surfactant TWEEN 20™, and 25 uG/uL calf thymus DNA was added to the pellet of white blood cells. The suspension was mixed and then heated at 100° C. for 5 minutes. After the suspension cooled to room temperature, 150 uL of ACES (2-[(2-amino-2-oxoethyl)-amino]ethanesulfonic acid) buffer was added, followed by the addition of 25 uL of a solution of polymer capture agent. The mixture was vigorously mixed, and then centrifuged at 14,000 rpm for 2 minutes at ambient temperature. The supernatant was removed and discarded. To the pellet containing the capture agent-DNA complex was added 100 uL of 20 mmolar sodium hydroxide and the mixture was then heated to 100° C. for 5 minutes to release the DNA. This solution (25 uL), without further treatment, was introduced directly into the PCR reagent mixture.

The leuco dye dispersion contained agarose (0.5%), 4,5-bis(4-dimethylaminophenyl)-2-(4-hydroxy-3-methoxyphenyl)imidazole leuco dye (250 μmolar), diethylenetriaminepentaacetic acid (100 μmolar), 4'-hydroxyacetanilide (5 mmolar), polyvinylpyrrolidone (112 mmolar) and sodium phosphate, monobasic, 1-hydrate (10 mmolar).

The conjugate solution used in this Example contained a conjugate (126 μL/L) of streptavidin and horseradish peroxidase obtained from commercial sources (Zymed Laboratories, Inc.), casein (0.5%) and merthiolate (0.5%) in phosphate buffered saline solution (24 mmolar sodium phosphate and 75 mmolar sodium chloride). The final conjugate concentration was 312 nG/mL.

The wash solution used in this example contained sodium chloride (373 mmolar), (ethylenedinitrilo)tetraacetic acid disodium salt (2.5 mmolar), decyl sodium sulfate (38 mmolar) and ethylmercurithiosalicylic acid, sodium salt (25 μmolar) in sodium phosphate, monobasic 1-hydrate buffer (25 mmolar, pH 7.4).

A "TP4" monoclonal antibody was used in the reaction mixture. This antibody is specific to DNA polymerase from *Thermus aquaticus* and is described in more detail in recently allowed U.S. Ser. No. 07/958,144 to Scalice et al., incorporated herein by reference. Generally, it was prepared from the immune cells of DNA polymerase immunized mice using conventional procedures, such as those described by Milstein et al, *Nature* 256, pp. 495–497, 1975 and hybridoma cell lines (either HB 11126 or 11127 from ATCC), whereby antibody secreting cells of the host animal were isolated from lymphoid tissue (such as the spleen) and fused with SP2/0-Ag14 murine myeloma cells in the presence of polyethylene glycol, diluted into selective media and plated in multiwell tissue culture dishes. About 7–14 days later, the hybridoma cells containing the antibodies were harvested, and purified using conventional techniques.

The polymerase chain reaction mixture (100 uL) contained tris(hydroxymethyl)aminomethane buffer (10 mmolar, pH 8), potassium chloride (50 mmolar), magnesium chloride (10 mmolar), dATP, dCTP, dGTP and dTTP (1.5 mmolar of each), primers (0.4 μmolar of each), gelatin (0.01%), the noted DNA polymerase (16 units/100 μL) and the "TP4" monoclonal antibody (50:1 molar ratio to DNA polymerase).

The remainder of the reagents and materials were obtained using commercial sources or prepared at Johnson & Johnson Clinical Diagnostics Company using conventional procedures.

Detection of Amplified HIV-I DNA

The PCR protocol of this invention included:

40 amplification cycles, each cycle of:

A) heating at 95° C. for 15 seconds for denaturation (195 seconds on first cycle only), and B,C) priming (annealing) and extension at 64° C. for 30 seconds.

The assay was carried out using 16 units of DNA polymerase/100 μL and 25 μL of the DNA extraction mixture, as indicated above, in the reaction mixture.

Detection of the amplification products was accomplished in the following manner. A portion (5 μL) of the final amplification reaction mixture was mixed with a buffer solution [tris(hydroxymethyl)aminomethane(10 mmolar, pH 8), potassium chloride (50 mmolar), magnesium chloride (10 mmolar) and gelatin (0.01%)](95 μL) and incubated at 95° C. for 5 minutes to denature the nucleic acids. The resulting solution was then transferred to SURECELL™ test devices so amplified target nucleic acids could be hybridized to the capture probes at 50° C.

The test wells of the test devices were then washed at 55° C. with a buffer solution [sodium dihydrogen phosphate (10 mmolar), sodium chloride (150 mmolar), sodium decyl sulfate (1%) and ethylenediaminetetraacetic acid (1 mmolar)] (250 μL, pH 7.4). The streptavidinperoxidase conjugate solution (50 μL) noted above was added to each test well and allowed to flow through the membrane at room temperature. After two minutes, the test wells were washed a second time.

The leuco dye dispersion (100 μL) noted above was added to each test well, and the devices were incubated at room temperature for two minutes. A solution (100 μL) of sodium azide (0.1%) was added to stop dye development.

The resulting dye signals observed in the assays were visually graded on a density scale of 0 to 10 (with 10 being the highest observed density). The results of the assays are shown below in Table 2.

TABLE 2

The results of amplification of DNA from leucocytes isolated from whole blood of patients according to the method of this invention. Detection of HIV-1 product.

| Specimen No. | Color Score | HIV serotype |
|---|---|---|
| 1 | 7.0 | positive |
| 2 | 7.5 | positive |
| 3 | 7.5 | positive |
| 4 | 6.5 | positive |
| 5 | 3.0 | positive |
| 6 | 7.5 | positive |
| 7 | 1.5 | positive |
| 8 | 7.0 | positive |
| 9 | 6.0 | positive |
| 10 | 7.5 | positive |
| 11 | 2.0 | negative |
| 12 | 2.0 | negative |

A color score of 2.0 or below based on internal controls represents a signal at the level of background. The color scores indicated that PCR had clearly occurred and the DNA from the target HIV-I had been amplified and detected.

The present invention has been described in detail with particular reference to preferred embodiments thereof, but it will be understood that variations and modifications can be effected within the spirit and scope of the invention.

All publications mentioned hereinabove are hereby incorporated by reference.

We claim:

1. A method for the selective preparation of leucocytes comprising:

A) mixing a whole blood sample with an erythrocyte lysing solution comprising between 50 mM and 100 mM of ammonium chloride and between about 0.001 weight percent to about 0.1 weight percent of a monocarboxylic acid or salt thereof selected from the group consisting of acetic acid, monosubstituted acetic acid, disubstituted acetic acid, and trisubstituted acetic acid, and wherein said lysing solution has a pH of between 6 and 8, B) centrifuging the resulting mixture to form a pellet of leucocytes from said whole blood sample, C) after removing the supernatant, washing said leucocyte pellet in a fresh sample of said lysing solution, and D) centrifuging and isolating said leucocyte pellet, provided that steps A) through D) are carried out within about 20 minutes.

2. The method of claim 1 wherein said monocarboxylic acid or salt thereof is between about 0.005 and 0.05 weight percent.

3. The method of claim 1 wherein said monocarboxylic acid or salt thereof is selected from the group consisting of monohalo acetic acid, dihalo acetic acid, trihalo acetic acid and acetic acid.

4. The method of claim 3 wherein said monocarboxylic acid is acetic acid.

5. The method of claim 1 wherein the pH is between 6.5 and 7.5.

6. The method of claim 1 wherein steps A) through D) are carried out within from about 10 to about 16 minutes.

7. The method of claim 1 wherein said whole blood sample has a volume of from about 0.01 to about 10 mL.

8. The method of claim 1 wherein each centrifugation step is carried out within less than about 10 minutes.

9. A method for the amplification and detection of a target nucleic acid comprising:

I) selectively preparing leucocytes suspected of containing a target nucleic acid in a whole blood sample by:

A) mixing a whole blood sample with an erythrocyte lysing solution comprising between 50 mM and 100 mM of ammonium chloride and between about 0.001 weight percent to about 0.1 weight percent of a monocarboxylic acid or salt thereof selected from the group consisting of acetic acid, monosubstituted acetic acid, disubstituted acetic acid and trisubstituted acetic acid, and wherein said lysing solution has a pH of between 6 and 8, B) centrifuging the resulting mixture to form a pellet of leucocytes from said whole blood sample, C) after removing the supernatant, washing said leucocyte pellet in a fresh sample of said lysing solution, and D) centrifuging and isolating said leucocyte pellet, provided that steps A) through D) are carried out within about 20 minutes, II) lysing the leucocytes in said washed pellet to release said target nucleic acid, III) amplifying said released target nucleic acid using polymerase chain reaction and a set of primers that are specific to and hybridizable with the opposing strands of said target nucleic acid, and IV) detecting said amplified target nucleic acid.

10. The method of claim 9 wherein steps A) through D) are carried out within from about 10 to about 16 minutes.

11. The method of claim 9 wherein said whole blood sample has a volume of from about 0.01 to about 10 mL.

12. The method of claim 9 wherein each centrifugation step is carried out within less than about 10 minutes.

13. The method of claim 9 wherein the polymerase chain reaction is carried out in the presence of a thermostable DNA polymerase and wherein one or both of said primers are labeled for detection.

14. The method of claim 13 wherein said labeled primers are labeled with biotin, and detection is achieved using a conjugate of avidin and an enzyme which can provide a detectable signal in the presence of its substrate.

15. The method of claim 9 for the detection of a viral, bacterial, fungal or protozoan RNA or DNA.

16. The method of claim 15 for the detection of RNA or DNA from any of a Streptococcus species, Mycobacterium species, Pneumocystis carinii, herpes simplex viruses, Epstein Barr virus, cytomegalovirus, hepatitis viruses, retroviruses, Candida species, or Aspergillus species.

17. The method of claim 16 for the detection of HIV-I, HIV-2, Mycobacterium tuberculosis, Mycobacterium avium complex or cytomegalovirus RNA or DNA.

18. The method of claim 9 wherein said amplified target nucleic acid is detected using, a reagent which provides a colorimetric or chemiluminescent signal in response to said label on said labeled primer.

19. A kit for polymerase chain reaction comprising:

a) a set of two primers specific to and hybridizable with opposing strands of a target nucleic acid, one or both of said primers being labeled with a detection moiety, and in the same or different package, at least one additional PCR reagent, and b) in a separate package, a solution or a dry composition containing, when said dry composition is reconstituted with water, between 50 mM and 100 mM of ammonium chloride and between about 0.001 weight percent to about 0.1 weight percent of a monocarboxylic acid or salt thereof selected from the group consisting of acetic acid, monosubstituted acetic acid, disubstituted acetic acid, and trisubstituted acetic acid, and wherein said solution has a pH of between 6 and 8.

20. The kit of claim 19, wherein one or both of said primers are labeled with biotin, and said kit comprises additionally a thermostable DNA polymerase cofactor which is a magnesium or manganese salt, and dATP, dCTP, dGTP, and dTTP.

21. The kit of claim 19, wherein said set of primers comprises two primers specific to and hybridizable with the opposing strands of HIV-I, HIV-2, Mycobacterium tuberculosis, Mycobacterium avium complex or cytomegalovirus DNA or RNA.

\* \* \* \* \*